United States Patent
Goldenshtein et al.

(10) Patent No.: US 7,800,062 B2
(45) Date of Patent: Sep. 21, 2010

(54) METHOD AND SYSTEM FOR THE EXAMINATION OF SPECIMEN

(75) Inventors: Alex Goldenshtein, Rishon LeZion (IL); Radel Ben-Av, Rehovot (IL); Asher Pearl, Kadima (IL); Igor Petrov, Holon (IL); Nadav Haas, Merkaz-Shapira (IL); Pavel Adamec, Haar (DE); Yaron Gold, Zicron-Yaacou (IL)

(73) Assignee: Applied Materials, Inc., Santa Clara, CA (US)

( * ) Notice: Subject to any disclaimer, the term of this patent is extended or adjusted under 35 U.S.C. 154(b) by 1220 days.

(21) Appl. No.: 10/912,792

(22) Filed: Aug. 6, 2004

(65) Prior Publication Data

US 2005/0116164 A1 Jun. 2, 2005

Related U.S. Application Data

(63) Continuation of application No. 10/390,979, filed on Mar. 17, 2003, which is a continuation of application No. 10/149,565, filed on Jun. 11, 2002, now abandoned.

(51) Int. Cl.
*G01B 15/04* (2006.01)
(52) U.S. Cl. .................... 250/310; 250/306; 250/307; 250/311; 250/396 R; 250/396 ML; 250/397
(58) Field of Classification Search ................ 250/306, 250/307, 310, 311, 396 R, 396 ML, 397
See application file for complete search history.

(56) References Cited

U.S. PATENT DOCUMENTS 3,930,181 A * 12/1975 Pfeiffer ................... 313/421
4,785,176 A * 11/1988 Frosien et al. ........ 250/396 ML (Continued)

FOREIGN PATENT DOCUMENTS

GB 2067348 A * 7/1981

(Continued)

OTHER PUBLICATIONS

"Local High Mag Scanning at Two Tail Ends of Low Mag Scanning for Creating High Mag SEM Stereo Images" IBM Technical Disclosure Bulletin, Sep. 1991, NB9109271.*

(Continued)

*Primary Examiner*—Robert Kim
*Assistant Examiner*—Michael Maskell
(74) *Attorney, Agent, or Firm*—Sonnenschein Nath & Rosenthal LLP

(57) ABSTRACT

The present invention provides, according to a first aspect, a method for the examination of specimen with a beam of charged particles. The method provides one or more images of the specimen made with different view angles, so that, compared to a single image of the specimen, a lot of additional information about the specimen can be accessed. The different view angles (angles of incidence) are achieved by tilting the beam between the two images and moving the specimen to a new position so that the displacement of the beam caused by the tilting of the beam is compensated. Accordingly, while displaying/recording the second image the beam scans over the same area as it has scanned while displaying/recording the first image.

17 Claims, 7 Drawing Sheets

U.S. PATENT DOCUMENTS

| | | | | |
|---|---|---|---|---|
| 4,983,832 A | * | 1/1991 | Sato | 250/310 |
| 5,644,132 A | * | 7/1997 | Litman et al. | 250/310 |
| 6,353,222 B1 | * | 3/2002 | Dotan | 250/310 |
| 6,452,175 B1 | * | 9/2002 | Adamec | 250/310 |

FOREIGN PATENT DOCUMENTS

| | | | |
|---|---|---|---|
| JP | 58137949 A | * | 8/1983 |
| JP | 10302703 A | * | 11/1998 |
| JP | 11-067130 | | 3/1999 |
| WO | WO 0145136 A1 | * | 6/2001 |

OTHER PUBLICATIONS

"Simultaneous Shift and Scan in an SEM Using SCAN Coils" IBM Technical Disclosure Bulletin, Jun. 1990, NA9006112.*

Applied Materials Israel, Ltd., JP Application No. P2006-032896; Notice of Reasons for Rejection; Jan. 19, 2010; 6pp.

Topcon Corp; JP Publication No. 11-067130 published Mar. 9, 1999; English Translation of document; 16pp.

* cited by examiner

METHOD AND SYSTEM FOR THE EXAMINATION OF SPECIMEN

RELATED APPLICATIONS

The present application is a continuation of application Ser. No. 10/390,979, entitled "Method and System For The Examination of Specimen", filed on Mar. 17, 2003, which is a continuation of application Ser. No. 10/149,565, filed Jun. 11, 2002, now abandoned. This patent application is hereby incorporated by reference in its entirety.

FIELD OF THE INVENTION

The invention relates to a method and a system for the examination of specimen. Especially, the invention relates to a method and a system for the examination of specimen with a beam of charged particles.

BACKGROUND OF THE INVENTION

The resolution of the conventional optical microscopy is limited by the wavelength of the visible light. Furthermore, at the highest resolution the conventional optical microscopy has a very shallow depth of field. These two limitations have led to the increased popularity of charged particle devices for the examination of specimen. Compared to optical light accelerated charged particles, for example electrons, do exhibit a shorter wavelength, which leads to an increased resolution power. Accordingly, charged particle beams, especially electron beams, are used in a variety of ways in biology, medicine, the materials sciences, and lithography. Examples include the diagnosis of human, animal, and plant diseases, visualization of sub cellular components and structures such as DNA, determination of the structure of composite materials, thin films, and ceramics, or the inspection of masks and wafers used in semiconductor technology.

Furthermore, charged particle devices are well suited for the examination of the microstructure of solid surfaces. Especially, the scanning electron microscope is a versatile instrument for examining the microstructure of a surface, because it combines high spatial resolution with depth of field in the same image, and requires only minimal sample preparation. Modern instruments distinguish features as small as 1 nm, while retaining crisp focus throughout tens of microns in the vertical direction. Hence, it is well suited for routine inspections of the intricate surface details of highly integrated circuits. Charged particle devices may, for example, be used in order to monitor the quality of the wafer processing in the semiconductor industry. Thereby, the device is actually located within the production environment, so that problems of the wafer processing are recognized as soon as possible.

However, conventional charged particle devices are not capable of providing accurate critical dimension, accurate height or accurate edge width measurements without the need of massive manual interference. In order to measure, for example, the height difference between two image points, usually two images are recorded with a defined specimen tilt between the exposures. However, mechanically tilting the specimen leads to a number of disadvantages. Due to mechanical imperfections a lateral movement of the specimen is inevitable which often results in misregistrations between the elements of a stereo image pair. Accordingly, additional alignments are necessary which slow down the process considerably. Furthermore, tilting large specimen, for example a 12 inch semiconductor wafer, requires a very robust and costly mechanical configuration in order to guarantee an adequate resistance of such a stage against vibrations.

In order to overcome the problems connected with a mechanical tilt of the specimen, it has been proposed to tilt the electron beam electrically in the electron-optical column to procure the same result, see e.g. B. C. Brenton et al. "A DYNAMIC REAL TIME 3-D MEASUREMENT TECHNIQUE FOR IC INSPECTION", Microelectronic Engineering 5 (1986) 541-545, North Holland or J. T. L. Thong et al. "In Situ Topography Measurement in the SEM", SCANNING Vol. 14, 65-72 (1992), FAMS, Inc. However, the height resolution of the proposed systems lies in the range of 75 to 100 nm, which is not sufficient for the requirements of the semiconductor industry.

Due to these problems, critical dimension measurements and side wall profiling are often done with an atomic force microscope. However, using an atomic force microscope requires an additional experimental setup which increases the costs significantly and is also very slow. Accordingly, there is a need for a faster and more automated method of examining a specimen which allows accurate critical dimension, accurate height or accurate edge width measurements.

SUMMARY OF THE INVENTION

The present invention provides a method for the examination of a specimen with a beam of charged particles. The method provides one or more images of the specimen made with different view angles, so that, compared to a single top view image of the specimen, a lot of additional information about the specimen can be accessed. The different view angles (angles of incidence) are achieved by tilting the beam between the two images and moving the specimen to a new position so that the displacement of the beam caused by the tilting of the beam is compensated. Accordingly, while displaying/recording the second image the beam scans basically over the same area as it has scanned while displaying/recording the first image. The present invention also provides an apparatus for the examination of specimen that is capable of performing this improved method.

By providing an oblique angle of incidence on the one hand and a corresponding movement of specimen on the other hand, stereo images of a specimen can be produced in a fast and reliable manner without the need for any additional alignments and without the need for excessive image processing. Accordingly, the additional information, which is contained in stereo images and which is extremely valuable in many cases, can be accessed without causing any additional costs.

According to a further aspect of the present invention, a method for directing a beam of charged particles onto the surface of a specimen under a predetermined angle of incidence is provided. The predetermined angle of incidence is achieved by the combined action of deflecting the beam away from the optical axis of an objective and focusing the beam onto the specimen. The deflection is done in at least two steps which are adjusted to each other so that the chromatic aberrations on the surface of the specimen are minimized. The present invention also provides a column for directing a beam of charged particles onto the surface of a specimen that is capable of performing this improved method.

It has been found by the present inventors that the chromatic aberrations caused by the first step of the deflection can be compensated to a large extent by the second step of the deflection if the two deflections are properly adjusted. The combined action of the two step deflection and focussing of the beam then leads to a resolution in the range of a few nanometers, which is comparable with the resolution that can be achieved without providing an oblique angle of incidence. The invention has thus the advantage that large angles of incidence on a specimen can be provided without a reduction in resolution arising from large chromatic aberrations.

According to a still further aspect of the present invention, methods are provided that allow an accurate measurement of important distances on the surface of a specimen, especially on the surface on a semiconductor wafer. These methods use a tilted beam of charged particles to get the information in a very fast and reliable manner.

BRIEF DESCRIPTION OF THE DRAWINGS

Some of the above indicated and other more detailed aspects of the invention will be described in the following description and partially illustrated with reference to the figures. Therein.

DESCRIPTION OF THE PREFERRED EMBODIMENTS

Figure 1:
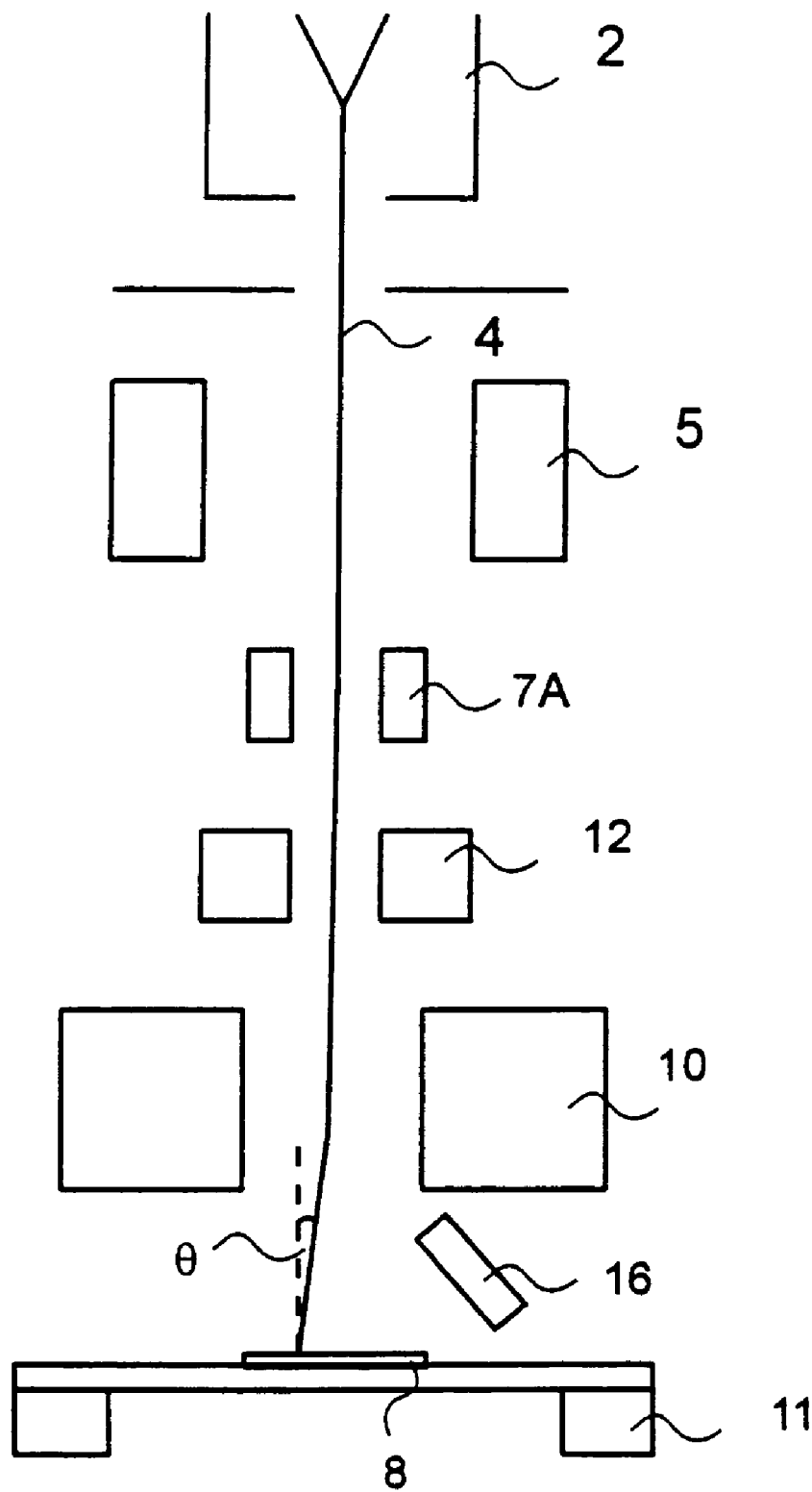
FIG. 1 is a schematic diagram of a charged particle apparatus according to a first embodiment of the present invention.

Preliminary, it should be appreciated by those skilled in the art that the present invention can be used with any charged particle device. However, for convenience the invention will be described with respect to its implementation in a scanning electron microscope (SEM). A preferred embodiment according to the invention is shown schematically in FIG. 1. The basic components of the device are an electron source 2, a lens system (condenser lens 5 and objective lens 10), scanning coils 12, beam shift coils 7A and a detector 16. In operation an electron beam 4 is emitted from the electron source 2. The electron source may, for example, be a tungsten-hairpin gun, a lanthanum-hexaboride gun, or a field-emission gun. The electrons are accelerated by an accelerating voltage supplied to the electron source 2. Since the beam diameter produced directly by the electron source usually is too large to generate a sharp image at high magnification, the electron beam 4 is guided through the condenser lens 5, which demagnifies the beam and leads the electron beam 4 towards a specimen 8.

The electron beam 4 then enters the field of the deflector 7A which deflects the electron beam 4 away from its path along the optical axis of the objective lens 10. The deflector 7A is followed by the scanning coils 12, which are used to move the electron beam 4 in a television-like raster over the surface of the specimen 8. After the scanning coils 12 the electron beam 4 enters the objective lens 10 that focuses the electron beam 4 onto the specimen 8. The objective lens 10 not only focuses the electron beam 4 but also rotates the electron beam 4. However, this effect is not shown, because it is difficult to depict in a two-dimensional drawing and because the skilled person is well aware of this additional effect.

Due to the combined action of the deflector 7A and the objective lens 10, the electron beam 4 hits the specimen under a predetermined angle of incidence, preferably in the range between 1° and 20° degrees. When the electrons strike the surface of the specimen 8, a variety of secondary products, such as electrons of different energy, X rays, light, and heat, as well as electrons scattered backward are produced. Many of these secondary products and/or the backscattered charged particles are used to produce the image of the specimen and to collect additional data from the specimen. A secondary product of major importance to examination or the image formation of specimens are secondary electrons that escape from the specimen 8 at a variety of angles with relatively low energy (3 to 50 eV). The secondary and the back scattered electrons reach the detector 16 and are measured. By scanning the electron beam over the specimen and displaying/recording the output of the detector 16 an image of the surface of the specimen 8 is formed.

The specimen 8 is supported on a stage 11 (specimen support) which is moveable horizontally in all directions, in order to allow the electron beam 4 to reach the target areas on the specimen which are to be examined. When the specimen 8 is viewed under an oblique angle of incidence, the electron beam does not hit the specimen along the optical axis but it is displaced from the optical axis. Therefore, the stage 11 performs a corresponding movement with the specimen 8 so that the electron beam hits the same area on the specimen that would have been hit if the electron beam had not been deflected by the beam shift coils 7A. When the deflection of the electron beam 4 and, accordingly, the angle of incidence is changed, for example to produce a pair of stereo images, the stage 11 again moves the specimen 8 to a new position so that the displacement of the beam caused by the tilting of the beam is compensated. Accordingly, any misregistration between the two images can basically be avoided.

By providing an oblique angle of incidence on the one hand and a corresponding movement of specimen on the other hand, stereo images of a specimen can be produced in a fast and reliable manner without the need for any additional alignments. Accordingly, the additional information, which is contained in stereo images and which is extremely helpful in many cases, can be accessed without causing any additional costs. Normally, both images of a stereo pair are produced using an oblique angle of incidence. However, depending on the application, one of the stereo images may also be produced by using a top view of the specimen ($\theta=0°$).

The embodiment shown in FIG. 1 uses a pre-lens deflector 7A in order to deflect the electron beam 4. The deflection of the electron beam 4 leads to an off-axis path of the beam through the objective lens 10 which gives rise to chromatic aberrations.

Figure 2:
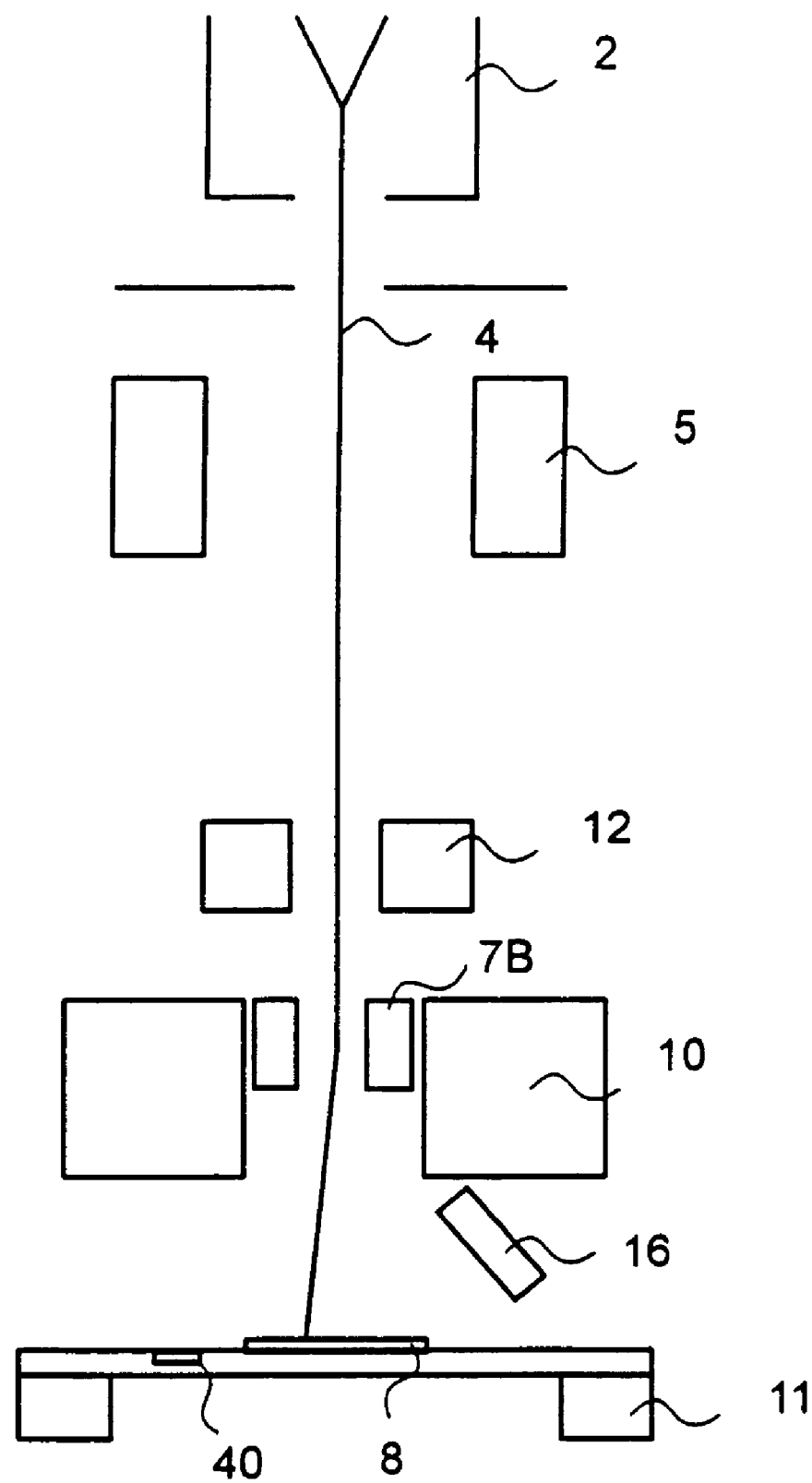
FIG. 2 is a schematic diagram of a charged particle apparatus according to a second embodiment of the present invention.

In order to decrease the chromatic aberrations, FIG. 2 shows a schematic diagram of an apparatus according to a further embodiment of the present invention. This embodiment is similar to that of FIG. 1, except for the following. The pre-lens deflector 7A has been replaced by an in-lens deflector 7B that is located within the objective lens 10. When the deflector 7B is placed inside the field of the objective lens 10, the chromatic aberrations are reduced considerably. The reduction can amount to 50% or more, if the deflector 7B is placed deep inside the field of the objective lens 10 or even partly below the objective lens 10.

In order to further improve the performance of the system, the embodiment shown in FIG. 2 contains a reference target 40 integrated into the stage 11. The reference target 40 is used to determine the precise angle of incidence of the electron beam 4 hitting the reference target 40. For example, the reference target may contain a repeating structure of lines or trenches which exhibit vertical walls. By moving the stage 11 so that the reference target 40 comes within the scanning range of the electron beam 4, images of the reference target 40 can be used to measure the angle of incidence and to find a parameter setting (for example for the deflector 7B, the objective lens 10, the beam energy, etc.) so that electron beam 4 hits the reference target 40 with predetermined angle of incidence. Once this parameter setting has been found, it can be used for precise measurements on the actual specimen 8 later on.

In the embodiment shown in FIG. 2 the reference target 40 is integrated into the stage 11. However, the reference target 40 might as well be provided on a separate support, which for example can be rotated in order to bring the reference target 40 within the scanning range of the electron beam 4. Furthermore, a heating system (not shown) can be provided for the reference target 40 so that by heating the reference target 40 contaminants present on the surface of the target are evaporated. By heating the reference target from time to time a clean reference target can be guaranteed over long period of time. Accordingly, the down time of the complete system can be reduced.

Figure 3:
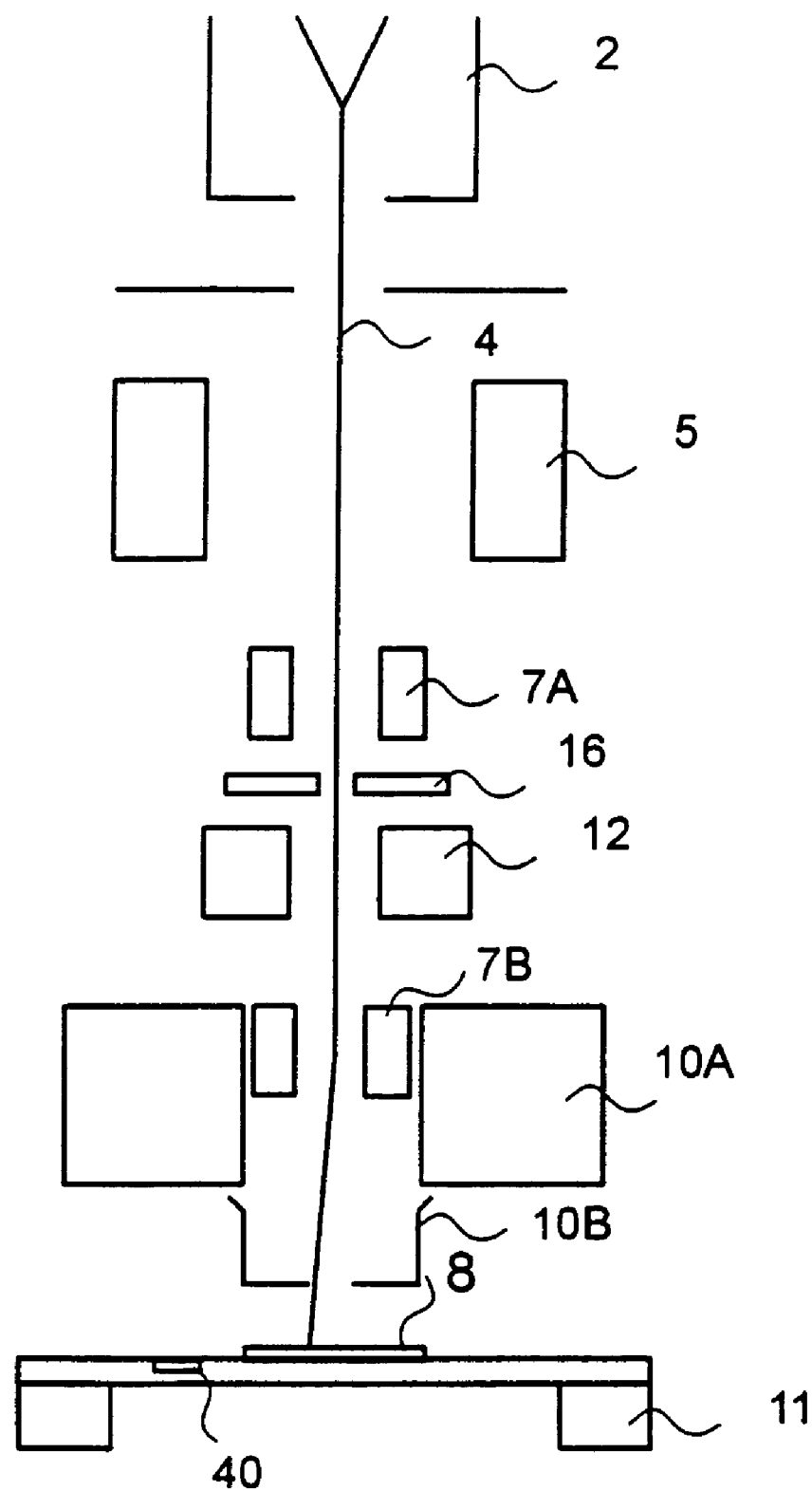
FIG. 3 is a schematic diagram of a charged particle apparatus according to a third embodiment of the present invention.

In order to further decrease the chromatic aberrations, FIG. 3 shows a schematic diagram of an apparatus according to a further embodiment of the present invention. This embodiment is similar to that of FIG. 1 and FIG. 2, except for the following. Instead of using either a pre-lens deflector 7A or an in-lens deflector 7B, the embodiment shown in FIG. 3 uses the pre-lens deflector 7A and the in-lens deflector 7B in combination. It has been found by the present inventors that the chromatic aberrations caused by a first deflector, in this example the pre-lens deflector 7A, can be compensated to a large extent by a second deflector, in this example the in-lens deflector 7B, if the deflections caused by these coils are properly adjusted. In the present example a pre-lens deflector 7A and an in-lens deflector 7B are used. However, it is also possible to use two pre-lens deflectors or two in-lens deflectors to achieve the same results.

The precise adjustment of the two deflections depends on a number of parameters, for example the chosen angle of incidence, the beam energy, the objective lens current, etc. However, the practice of the invention does not depend on a precise knowledge of these parameters and their effects on the chromatic aberrations caused by the beam deflection. The direction of the deflection and the angle of deflection of the pre-lens and the in-lens deflector at which for a preselected angle of incidence minimum aberration is obtained may be extracted experimentally from the resulting images, either from the images of the specimen 8 itself or from images of the reference target 40. The combined action of the pre-lens deflector and the in-lens deflector then lead to a resolution in the range of a few nanometers, which is comparable with the resolution that can be achieved without providing an oblique angle of incidence. The invention has thus the advantage that large angles of incidence on a specimen can be provided without a reduction in resolution arising from large chromatic aberrations.

In order to further improve the performance of the system, the embodiment shown in FIG. 3 contains an objective lens 10 which is a combination of a magnetic lens 10A and an electrostatic lens 10B. Accordingly, the objective lens 10 is a compound magnetic-electrostatic lens. Preferably, the electrostatic part of the compound magnetic-electrostatic lens 10 is an electrostatic retarding lens 10B. Using such a compound magnetic-electrostatic lens 10 yields superior resolution at low acceleration energies, such as a few hundred electron volts in the case of a SEM. Such low acceleration energies are desirable, especially in modern semiconductor industry, to avoid charging and/or damaging of radiation sensitive specimens.

Figure 4:
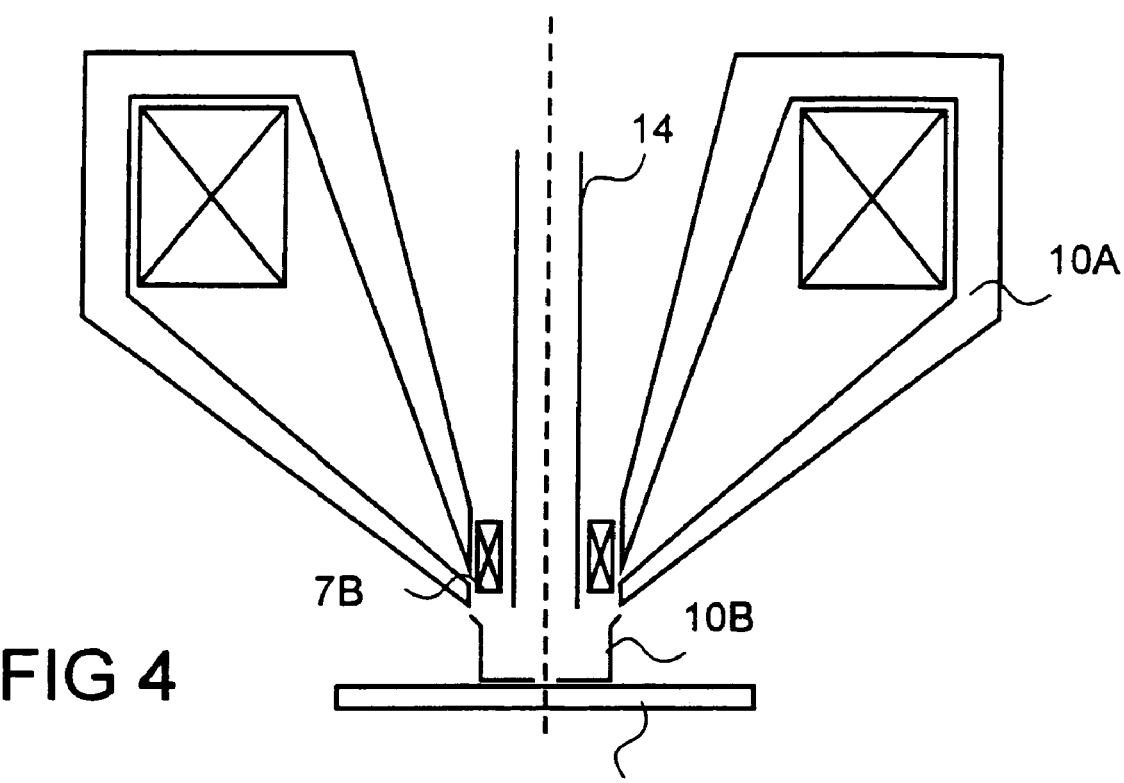
FIG. 4 is an enlarged view showing the objective lens of the embodiment of FIG. 3.
Figure 5:
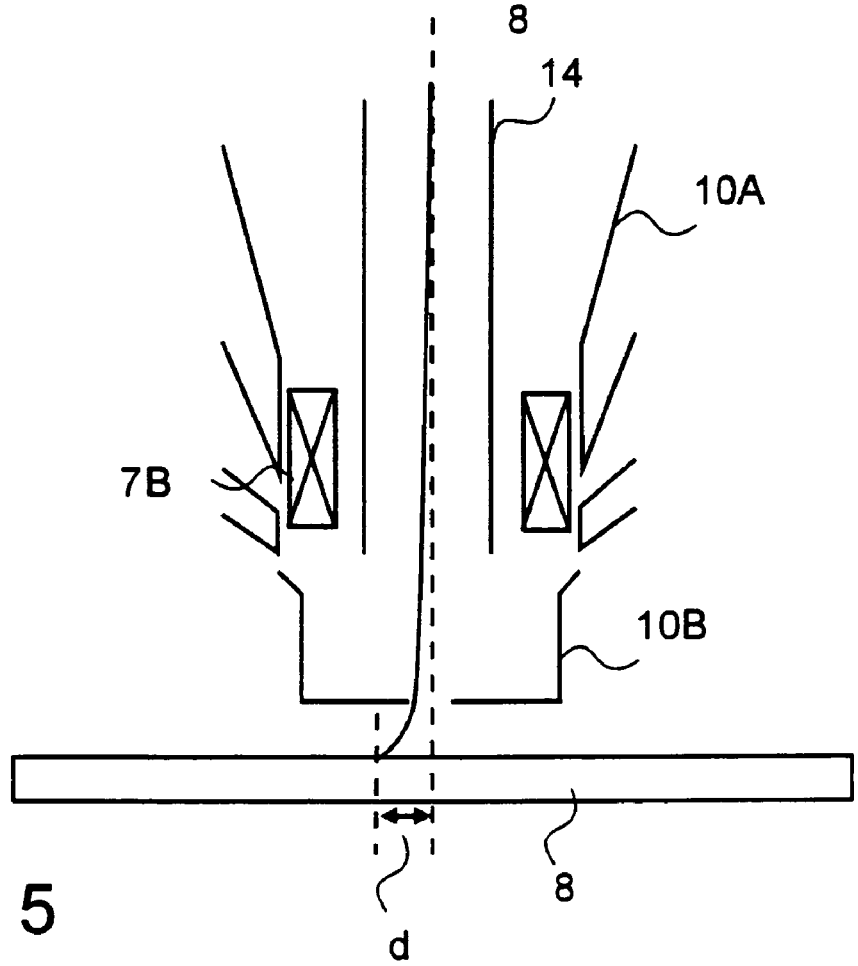
FIG. 5 is an enlarged view of FIG. 4.

FIGS. 4 and 5 show enlarged views on the compound magnetic-electrostatic lens 10 and the specimen 8 as shown in FIG. 3. To achieve a small focal length, the magnetic flux generated by a current through an excitation coil is conducted through pole pieces and is concentrated into a small region along the optical axis of the magnetic lens. The magnetic field is rotational symmetric around the optical axis and reaches its maximum value in the pole gap between the upper and the lower pole piece. Furthermore, the beam shift coils 7B are placed inside the magnetic field of the objective lens 10A, so that there is considerable overlap between their respective fields.

In addition to the magnetic lens 10A the embodiment shown in FIGS. 3 to 5 contains an electrostatic retarding lens which is situated close to magnetic lens 10A. The electrostatic retarding lens 10B has two electrodes held at different potentials. In the illustrated embodiment one of the two electrodes is formed by a cylindrical beam tube 14 which is arranged within the magnetic lens 10A along the optical axis. The second electrode of the electrostatic retarding lens 10B is a metallic cup provided below the magnetic lens 10A. In operation of the system the first electrode is usually held at high positive potential, for example 8 kV, where as the second electrode is held at lower positive potential, for example 3 kV, so that the electrons are decelerated in the corresponding electrostatic field from a first energy to lower second energy.

In the example shown in FIGS. 4 and 5 the specimen 8 is held at ground potential. Accordingly, there is a further electrostatic retarding field between the metallic cup and the specimen 8. Due to the electrostatic retarding field between the metallic cup and the specimen 8, an initial deflection of the electron beam 4 caused by the beam shift coils 7A and 7B is enhanced leading to an increased angle of incidence. Accordingly, in order to achieve a predetermined angle of incidence only small deflections caused by the beam shift coils 7A and 7B are necessary.

The surface of the specimen need not be grounded. The electric potential on the surface of the specimen may also be adjusted by applying a voltage to the specimen. A voltage can be applied to a wafer, for example, in order to obtain voltage contrast imaging which is used to detect shorts in a circuit. As long as the potential of the metallic cup is higher than the potential on the surface of the specimen, an electrostatic retarding field is produced.

As can be seen from FIG. 5, when the specimen 8 is viewed under an oblique angle of incidence $\theta$, as measured with regard to an axis normal to the surface of the specimen, the electron beam does not hit the specimen along the optical axis of the objective lens 10. The electron beam 4 is displaced from the optical axis by a distance d. Therefore, the stage 11 performs a corresponding movement with the specimen 8 so that the electron beam hits the same area on the specimen that would have been hit, if the electron beam had not been deflected by the beam shift coils 7A. When the deflection of the electron beam 4 and, accordingly, the angle of incidence θ is changed, for example to −θ, the stage 11 again moves the specimen 8 to a new position so that any misregistration between the two images can basically be avoided.

Figures 6A, 6B:
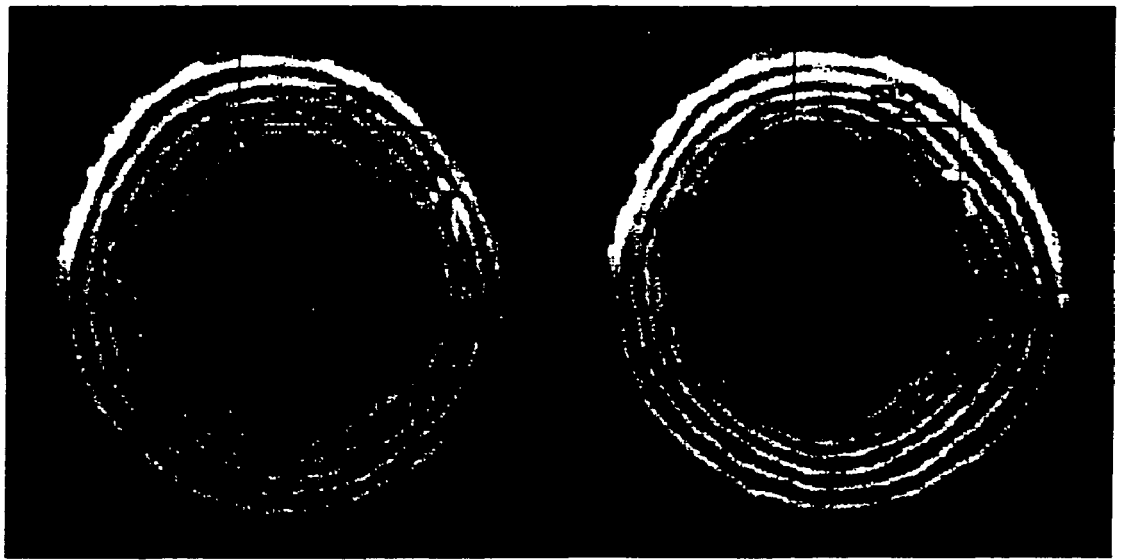
FIG. 6A and FIG. 6B show a pillar which extends from a flat surface and whose height is to be determined.

FIG. 6A and FIG. 6B together with following description will explain how according to the present invention an accurate height measurement is performed. FIG. 6A and FIG. 6B show a pillar which extends from a flat surface. FIG. 6A is an image of the pillar taken with a beam tilt of $\theta_L=-3°$ whereas FIG. 6B is an image of the pillar taken with a beam tilt of $\theta_R=+3°$ with respect to an axis normal to the flat surface.

To determine the height difference Δh between the top of the pillar and the bottom surface a distinctive feature has to be located for each level. On top of the pillar the right end of a flake was used as the first distinctive feature. On the bottom surface the end of a particle was used as the second distinctive feature. In both images the distance in X-direction between the two features is measured, P1 for FIG. 6A and P2 for FIG. 6B. The difference P between the distance P1 and the distance P2 (P=P1−P2, P is called the parallax) is then used in order to calculate the height difference Δh between the top of the pillar and the bottom surface. The height difference Δh is given by the formula:

$$\Delta h = P*((\sin\theta_R * \sin\theta_L)/(\sin\theta_R - \sin\theta_L))$$

For small angle approximation ($\theta_R$, $\theta_L \leq 5°$) the height difference can also be given by:

$$\Delta h = P/(2*\sin((\theta_R-\theta_L)/2)).$$

In the example shown in FIGS. 6A and 6B the distance P1 corresponds to 0.546 μm whereas the distance P2 corresponds to 0.433 μm. Accordingly, the height difference Δh between the top of the pillar and the bottom surface in this example is 1.079 μm.

Due to the present invention it does not take any extra effort to gain additional height information from the specimen. However, this additional information is often extremely valuable, particularly on specimens whose topography is complex. In this example the height of a pillar was determined, It is clear, however, that the same procedure can also be used to determine the depth of a trench or a hole. In the case of a semiconductor wafer the accurate depth of a trench, for example the depth of an isolation trench, or the accurate depth of a contact holes, is extremely useful information in order to control the quality of the production process.

Figures 7A, 7B:
FIG. 7A and FIG. 7B show a contact hole which is extending downward from a flat surface and whose width at its bottom is to be determined.

Once the depth of a trench or a hole or the height of a line is known, this information can be used in order to determine further interesting features. For example, by knowing the depth of a contact hole, a further embodiment of the present invention can be used, in order to determine the true width of the contact hole at its bottom. FIG. 7A and FIG. 7B show a contact hole extending downward from a flat surface. FIG. 7A is an image of the contact hole taken with a beam tilt of $\theta_L=-3°$ whereas FIG. 7B is an image of the contact hole taken with a beam tilt of $\theta_R=+3°$ with respect to an axis normal to the flat surface.

In FIG. 7A (left view) the left top edge $T_1$, the right top edge $T_2$ and the right bottom edge $B_L$ of the contact hole can be seen. In FIG. 7B (right view) again the left top edge $T_1$ and the right top edge $T_2$ can be seen. Furthermore, the left bottom edge $B_R$ of the contact hole is visible. By measuring the visible distances $T_1B_L$ and $T_1T_2$ as measured in FIG. 7A, the left view, and the distance $T_2B_R$ as measured in FIG. 7B, the right view, the true width $W_b$ of the contact hole at its bottom can be calculated:

$$W_b = T_1B_L/\cos\theta_L + T_2B_R/\cos\theta_R + h(\tan\theta_L + \tan\theta_R) - W_t$$

where h is the depth of the contact hole and $W_t$ is the width of the contact hole at the top. In the present example $W_t$ is given by $T_1T_2/\cos\theta L$. In the example shown in FIGS. 7A and 7B the distance $T_1B_L/\cos\theta L$ corresponds to 0.29 μm, the distance $T_2B_R/\cos\theta R$ corresponds to 0.334 μm and the distance $T_1T_2/\cos\theta L$ corresponds to 0.4005 μm. Furthermore, the depth h of the contact hole was determined to be 1.0 μm. Accordingly, the true width $W_b$ of the contact hole at its bottom in this example is 0.324 μm.

The method has the advantage that true width W of the contact hole at its bottom can be determined even for contact holes having high aspect ratio (deep and narrow). This is in contrast to other methods, like the atomic force microscopy, which exhibit extreme difficulties in these cases.

In addition to the determination of the true width W of the contact hole at its bottom, a further embodiment of the present invention can be used, in order to determine the width of a sidewall which is visible in the FIG. 7A or 7B. For example, from FIG. 7B the width of the left sidewall of the contact hole can be determined. The width of the sidewall in this context means the lateral distance in horizontal wafer plane direction between the top of the sidewall and the bottom of the sidewall. By measuring the visible distance $T_2B_R$ as measured in FIG. 7B the true width $W_L$ of the left sidewall of the contact hole can be calculated:

$$W_L = W_t - T_2B_R/\cos\theta_R - h\tan\theta_R$$

where $T_2B_R$ is the visible distance as measured between the bottom edge of the sidewall and the top edge on the opposite side of the trench or hole, h is the depth of the trench or hole, $W_t$ is the width of the trench or hole at the top of the trench or the hole, and $\theta_R$ is the viewing angle of the image of FIG. 7B.

Similarly, by measuring the visible distance $T_1B_L$ as measured in FIG. 7A the true width $W_R$ of the left sidewall of the contact hole can be calculated:

$$W_R = W_t - T_1B_L/\cos\theta_L - h\tan\theta_L$$

where $T_1B_L$ is the visible distance as measured between the bottom edge of the sidewall and the top edge on the opposite side of the trench or hole, h is the depth of the trench or hole, $W_t$ is the width of the trench or hole at the top of the trench or the hole, and $\theta_L$ is the viewing angle of the image of FIG. 7A.

Figures 8A, 8B:
FIG. 8A and FIG. 8B show a line which is extending upward from a flat surface and whose width at its bottom is to be determined.

According to a further embodiment of the present invention, by knowing the height of a line a pair of stereo images of that line can be used in order to determine the true width of the line at its bottom. FIG. 8A, the left view, and FIG. 8B, the right view, show a line extending upward from a flat surface. FIG. 8A is an image of the line taken with a beam tilt of $\theta_L=-3°$ whereas FIG. 8B is an image of the line taken with a beam tilt of $\theta_R=+3°$ with respect to an axis normal to the flat surface.

In FIG. 8A the left bottom edge $X_1$, the left top edge $X_2$ and the right top edge $X_3$ of the line can be seen. In FIG. 8B again the left top edge $Y_3$ and the right top edge $Y_2$ can be seen. Furthermore, the right bottom edge $Y_1$ of the line is visible. By measuring the visible distances $X_1X_2$ and $X_2X_3$ as measured in FIG. 8A and the visible distances $Y_1Y_2$ and $Y_2Y_3$ as measured in FIG. 8B the true width $W_b$ of the line at its bottom can be calculated:

$$W_b = (X_1X_2+X_2X_3)/\cos\theta_L + (Y_1Y_2+Y_2Y_3)/\cos\theta_R - h(\tan\theta_L+\tan\theta_R) - W_t$$

or $$(X_1X_2+X_2X_3=X_1X_3,\ Y_1Y_2+Y_2Y_3=Y_1Y_3)$$

or $$W_b=X_1X_3/\cos\theta_L+Y_1Y_3/\cos\theta_R h(\tan\theta_L+\tan\theta_R)-W_t$$

where h is the height of the line and $W_t$ is the width of the feature at the top of the feature. For example, $W_t$ is given by $Y_2Y_3/\cos\theta_R$. In the example shown in FIGS. 8A and 8B the distance $(X_1X_2+X_2X_3)/\cos\theta_L$ corresponds to 0.274 µm, the distance $(Y_1Y_2+Y_2Y_3)/\cos\theta_R$ corresponds to 0.312 µm and the distance $Y_2Y_3/\cos\theta_R$ corresponds to 0.232 µm. Furthermore, the depth h of the line was determined to be 0.8 µm. Accordingly, the true width $W_b$ of the line at its bottom in this example is 0.27 µm.

Instead of the above presented formula, further equivalent formula can also be used, for example:

$$W_b=X_1X_2/\cos\theta_L+(Y_1Y_2+Y_2Y_3)/\cos\theta_R h(\tan\theta_L+\tan\theta_R)$$

or $$W_b=(X_1X_2+X_2X_3)/\cos\theta_L+Y_1Y_2/\cos\theta_R-h(\tan\theta_L+\tan\theta_R)$$

or $$W_b=X_1X_2/\cos\theta_L+Y_1Y_2/\cos\theta_R-h(\tan\theta_L+\tan\theta_R)+W_t.$$

Again, this method has the advantage that true width W of the line at its bottom can be determined even for lines having high aspect ratio (high and narrow). This is in contrast to other methods, like the atomic force microscopy, which exhibit extreme difficulties in these cases.

In addition to the determination of the true width W of the line at its bottom, a further embodiment of the present invention can be used, in order to determine the width of a sidewall which is visible in the FIG. 8A or 8B. For example, from FIG. 8B the width of the right sidewall of the line can be determined. The width of the sidewall in this context means the lateral distance in horizontal direction between the top of the sidewall and the bottom of the sidewall. By measuring the visible distance $Y_1Y_2$ as measured in FIG. 8B the true width $W_R$ of the right sidewall of the line can be calculated:

$$W_R=Y_1Y_2/\cos\theta_R-h\tan\theta_R$$

where $Y_1Y_2$ is the visible distance as measured between the bottom edge and the top edge of the sidewall of the feature, h is the height of the feature, and OR is the viewing angle of the image of FIG. 8B.

Similarly, by measuring the visible distance $X_1X_2$ as measured in FIG. 8A the true width $W_L$ of the left sidewall of the line can be calculated:

$$W_L=X_1X_2/\cos\theta_L-h\tan\theta_L$$

where $X_1X_2$ is the visible distance as measured between the bottom edge and the top edge of the sidewall of the feature, h is the height of the feature, and $\theta_L$ is the viewing angle of the image of FIG. 8A.

Figures 9A, 9B:
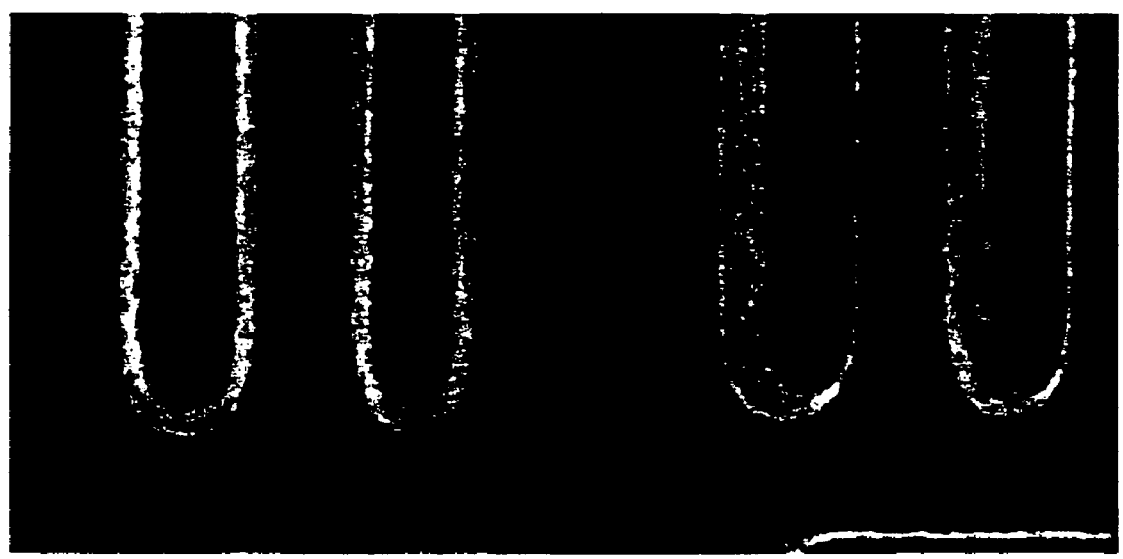
FIG. 9A and FIG. 9B show a top view and a tilt view of a trench present on the surface of a wafer.

FIG. 9A and FIG. 9B show a top view and a tilt view of a trench present on the surface of a wafer. As can be seen from FIG. 9B, the tilt view makes it possible to see and to define the true character of the sidewall of the trench. In the tilt view the sidewall can be seen much better and with significantly more details which are undetectable in FIG. 9A, the top view. Accordingly, a sidewall profile of the left sidewall of the trench can be compiled from FIG. 9B. Furthermore, by looking at same edge portions in both images, it is easy to see that the edge in the tilt view captures about twice as many pixels as in the top view. Obviously, this leads to a measurement of the edge width having a significantly better accuracy.

Figures 10A, 10B:
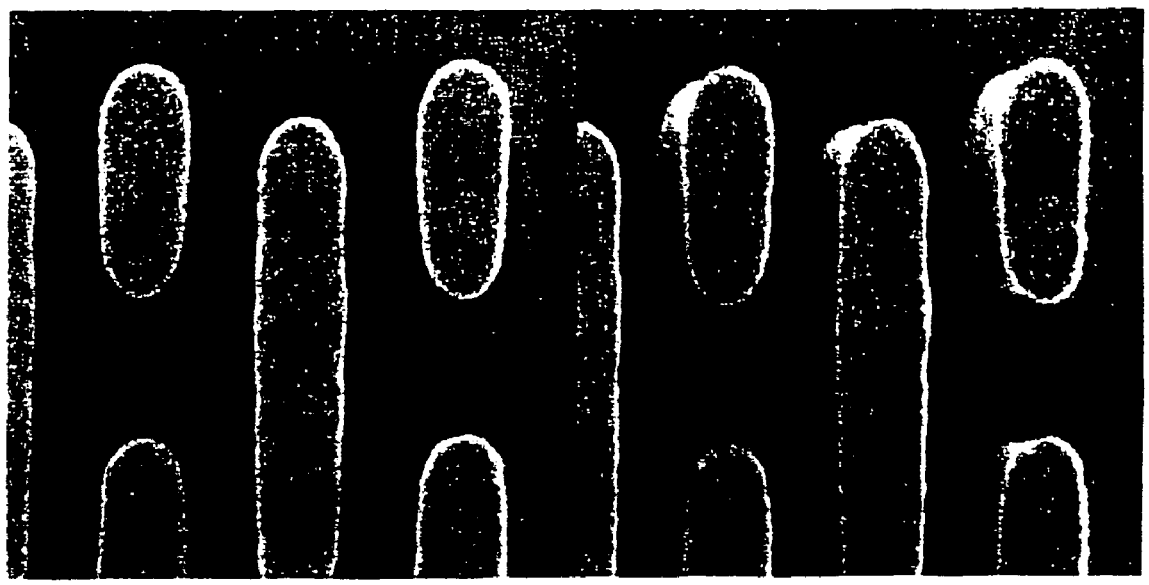
FIG. 10A and FIG. 10B show a top view and a tilt view of a line present on the surface of a wafer.

FIG. 10A and FIG. 10B show a top view and a tilt view of a line present on the surface of a wafer. Again, the tilt view (FIG. 10B) makes it possible to see and to define the true character of the sidewall of the line. In the tilt view the side wall can be defined as T-top and its profile can be determined. In the top (FIG. 10A) the T-top is undetectable.

While the invention has been described with reference to various exemplary embodiments thereof, those of ordinary skill in the art would appreciate that various implementations and variations are possible without departing from the scope and spirit of the invention, as defined by the appended claims. For example, it should be readily apparent that angles and the height and width dimension presented with regard to FIGS. 6 to 8 are only examples and that other angles, height and width dimension can be used. Similarly, the configuration of the objective lens is provided as example only, and other configurations of the objective lens may be used.

The invention claimed is:

1. A method for the examination of a specimen with a beam of charged particles, said method comprising the steps of:
   a) while the specimen is in a first position, scanning the beam over the specimen, to produce a first image, wherein during the scanning the beam is maintained in a first orientation so as to be incident upon a surface of the specimen at a first angle of incidence;
   b) tilting the beam and moving the specimen to a second position so that the beam is incident upon the surface of the specimen at a second angle of incidence and a displacement of the beam caused by the tilting of the beam is thereby compensated, wherein the tilting of the beam is achieved by combined actions of deflecting the beam away from an optical axis of an objective and focusing the beam onto the specimen wherein the beam is deflected in two steps which are adjusted with respect to each other so that chromatic aberrations on the surface of the specimen are minimized; wherein a first one of the two steps occurs before the beam enters the field of the objective and a second one of the two steps occurs when the beam is inside the field of the objective; and
   c) while the specimen is in the second position, scanning the beam over the specimen to produce a second image, wherein during the scanning the beam is maintained in a second orientation so as to be incident upon the surface of the specimen at the second angle of incidence.

2. The method according to claim 1 wherein deflection of the beam occurs before the beam enters a field of the objective.

3. The method according to claim 1 wherein deflection of the beam occurs inside a field of the objective.

4. The method according to claim 1 wherein the first and second images are used to measure height differences on the specimen.

5. The method according to claim 1 wherein the first and second images are used to measure a width of a feature recessed in the surface of the specimen.

6. The method according to claim 1 wherein the first and second images are used to measure a width of a feature protruding from the surface of the specimen at a bottom of the feature.

7. The method according to claim 1 wherein the first and second images are used to compile a stereoscopic image of the surface of the specimen.

8. The method according to claim 1 wherein the first and second images are used to produce a 3-dimensional representation of a feature of the specimen.

9. The method according to claim 1 wherein the first and second images are used to measure a width of an edge of a feature of the specimen.

10. The method according to claim 1 wherein the first and second images are used to compile a sidewall profile of a feature of the specimen.

11. The method according to claim 10 wherein a reference target is provided in order to determine a precise angle of incidence.

12. A charged particle apparatus for examining a specimen, the apparatus comprising:
 a) a particle source configured to provide a beam of charged particles;
 b) an objective configured to focus the beam of charged particles onto the specimen;
 c) a detector configured to measure at least one secondary product and/or backscattered particles coming from the specimen;
 d) at least one deflector configured to maintain the beam in a first orientation so as to be incident upon a surface of the specimen at a first angle of incidence, tilt the beam so that the beam is incident upon the surface of the specimen at a second angle of incidence, and maintain the beam in a second orientation so as to be incident upon the surface of the specimen at the second angle of incidence, wherein the deflector is further configured to deflect the beam of charged particles away from an optical axis of the objective so that by combined action of the deflector and the objective the beam of charged particles is tilted and is incident upon the surface of the specimen at the first or second angle of incidence;
 e) a specimen support configured to move the specimen from a first position to a second position so that a displacement of the beam caused by the tilting of the beam is compensated; and
 f) a scanning unit configured to scan the beam of charged particles over the specimen while the specimen is in the first position so that a first image is generated, and configured to scan the beam of charged particles over the specimen while the specimen is in the second position so that a second image generated wherein the apparatus comprises two deflectors which are adjusted with respect to each other so that chromatic aberrations on the surface of the specimen are minimized; wherein a first one of the deflectors is located before the objective outside a field of the objective and a second one of the deflectors is located within the field of the objective.

13. The apparatus according to claim 12 wherein the deflector is located before the objective outside a field of the objective.

14. The apparatus according to claim 12 wherein the deflector is located within a field of the objective.

15. The apparatus according to claim 12 wherein the objective is a combination of a magnetic lens and an electrostatic lens.

16. The apparatus according to claim 15 wherein an electrostatic retarding field is provided between the electrostatic lens and the specimen.

17. The apparatus according to claim 16 wherein a reference target is provided in order to determine a precise angle of incidence.

* * * * *